US011112376B2

(12) United States Patent
Hughes

(10) Patent No.: US 11,112,376 B2
(45) Date of Patent: Sep. 7, 2021

(54) SYSTEMS AND METHODS FOR ELECTROCHEMICAL TRIGLYCERIDES ASSAYS

(71) Applicant: Polymer Technology Systems, Inc., Indianapolis, IN (US)

(72) Inventor: Gary L. Hughes, Camby, IN (US)

(73) Assignee: POLYMER TECHNOLOGY SYSTEMS, INC., Whitestown, IN (US)

(*) Notice: Subject to any disclaimer, the term of this patent is extended or adjusted under 35 U.S.C. 154(b) by 0 days.

(21) Appl. No.: 15/485,871

(22) Filed: Apr. 12, 2017

(65) Prior Publication Data
US 2017/0299539 A1 Oct. 19, 2017

Related U.S. Application Data

(60) Provisional application No. 62/322,093, filed on Apr. 13, 2016.

(51) Int. Cl.
*G01N 27/327* (2006.01)
*C12Q 1/00* (2006.01)
*G01N 33/543* (2006.01)
*G01N 33/92* (2006.01)

(52) U.S. Cl.
CPC ......... *G01N 27/3272* (2013.01); *C12Q 1/005* (2013.01); *G01N 33/5438* (2013.01); *G01N 33/92* (2013.01); *G01N 2333/902* (2013.01); *G01N 2333/90203* (2013.01); *G01N 2333/9121* (2013.01); *G01N 2333/91215* (2013.01); *G01N 2333/92* (2013.01)

(58) Field of Classification Search
CPC .......... G01N 27/3272; G01N 33/5438; G01N 33/92; C12Q 1/005
See application file for complete search history.

(56) References Cited

U.S. PATENT DOCUMENTS

| 4,223,090 A | 9/1980 | Mazza |
| 4,245,041 A | 1/1981 | Denney |
| 5,019,505 A | 5/1991 | Ferguson et al. |
| 8,187,453 B2 | 5/2012 | Wallace-Davis et al. |
| 2008/0268421 A1 | 10/2008 | Wallace-Davis et al. |
| 2015/0177178 A1 | 6/2015 | Duvall et al. |

FOREIGN PATENT DOCUMENTS

| CN | 101076601 A | 11/2007 |
| CN | 101918584 A | 12/2010 |
| WO | WO-2014037372 A1 * | 3/2014 |

OTHER PUBLICATIONS

W.-Y. Liao, et al. "Detection of triglyceride using an iridium nano-particle catalyst based amperometric biosensor", The Analyst, 133(12): p. 1757-1763 (Year: 2008).*

(Continued)

*Primary Examiner* — J. Christopher Ball
(74) *Attorney, Agent, or Firm* — Haynes and Boone, LLP

(57) ABSTRACT

A system for the electrochemical detection of triglyceride levels includes a test strip including an electrode and a counter electrode, the electrode and counter electrode located proximate to a sample reception area; and a coating on one of the electrode and counter electrode, the coating including a reagent coating for triglycerides.

10 Claims, 2 Drawing Sheets

(56) References Cited

OTHER PUBLICATIONS

Lapenaite, et al. "Current Trends in Enzymatic Determination of Glycerol", Critical Reviews in Analytical Chemistry, 36(1): p. 13-25, Jan. 2006.*
S.J. Sadeghi, "Amperometric Biosensor" in Encyclopedia of Biophysics, G.C.K. Roberts (Ed.), Springer, Berlin, Heidelberg, p. 61-67. (Year: 2013).*
S.-P. Chen, et al., "Lab-on-a-chip for analysis of triglycerides based on a replaceable enzyme carrier using magnetic beads". Analyst, 135(11): p. 2979-2986 (Year: 2010).*
International Search Report and Written Opinion issued in related PCT App. No. PCT/US2017/027180 dated Aug. 16, 2017 (14 pages).
Office Action issued in related Chinese Patent App. No. 201780035872.3 dated Sep. 4, 2020 (24 pages with English translation).
Extended European Search Report dated Nov. 12, 2019 issued in related European app. No. 17783046.0 (10 pages).
Feldbrugge R et al.: "Development and practical evaluation of an amperometric triglyceride sensor", Sensors and Actuators B: Chemical, Elsevier BV, NL, vol. 19, No. 1-3, Apr. 1, 1994 (Apr. 1, 1994), pp. 365-367, XP026570837, ISSN: 0925-4005, DOI: 10.1016/0925-4005(93)00998-E [retrieved on Apr. 1, 1994].
Laurinavicius V et al.: "Amperometric glyceride biosensor", Analytica Chimica Acta, Elsevier, Amsterdam, NL, vol. 330, No. 20-3, Sep. 10, 1996 (Sep. 10, 1996), pp. 159-166, XP002659859, ISSN: 0003-2670, DOI: 10.1016/0003-2670(96)00114-6 [retrieved on Dec. 12, 1998].

* cited by examiner

SYSTEMS AND METHODS FOR ELECTROCHEMICAL TRIGLYCERIDES ASSAYS

CROSS-REFERENCE TO RELATED APPLICATIONS

This application claims the benefit of Provisional Application No. 62/322,093 filed on Apr. 13, 2016, titled "Systems and Methods For Electrochemical Triglycerides Assays" the entire disclosure of which is hereby incorporated by reference.

BACKGROUND

The level of certain analytes in blood and other body fluids can predict disease or risk thereof. For example, the amounts of cholesterol and triglycerides in blood are a significant indicator of risk of coronary heart disease ("CHD"). Excess triglycerides in plasma are called "hypertriglyceridemia," and are linked to the occurrence of atherosclerosis and CHD in some people. Elevated triglycerides may be a consequence of other diseases, such as untreated diabetes mellitus. Like cholesterol, increases in triglyceride levels can be detected by plasma measurements.

The analysis of triglycerides may be performed according to various techniques. Laboratory tests are commonly used; however, such tests typically require taking a vial of blood, and results may take a significant amount of time to process. Additionally, electrochemical and reflectance based test strips that provide for testing in a point-of-care setting may be used.

BRIEF SUMMARY

In one embodiment, a reagent mixture for an electrochemical triglyceride sensor includes a surfactant and a triglyceride hydrolyzing reagent. The reagent mixture further includes Glycerol kinase and Glycerol-3-phosphate dehydrogenase. The reagent mixture further includes a coenzyme and a redox agent capable of being oxidized or reduced to form a product. In one alternative, the triglyceride hydrolyzing reagent is lipoprotein lipase. In another alternative, the coenzyme is nicotinamide adenine dinucleotide (NAD). Optionally, the surfactant includes a bile acid derivative. Alternatively, the surfactant includes a salt of a bile acid derivative. In one alternative, the bile acid derivative is selected from a list of bile acids that include: 5-Cholenic acid-3β-ol; 5α-Cholanic acid-3α-ol-6-one 3-acetate methyl ester; 5β-Cholanic acid 3,7-dione methyl ester; 5β-Cholanic acid; 5β-Cholanic acid-3α, 12α-diol 3-acetate methyl ester; Chenodeoxycholic acid; Cholic acid; Deoxycholic acid; Glycoursodeoxycholic acid; Hyodeoxycholic acid methyl ester; Hyodeoxycholic acid; Lithocholic acid; Sodium cholate hydrate; Sodium deoxycholate; Sodium glycochenodeoxycholate; Sodium taurochenodeoxycholate; Sodium taurocholate hydrate; Taurocholic acid sodium salt hydrate; and Ursodeoxycholic acid. Alternatively, the reagent mixture further includes Diaphorase.

In one embodiment, a system for the electrochemical detection of triglyceride levels includes a test strip including an electrode and a counter electrode, the electrode and counter electrode located proximate to a sample reception area and a coating on one of the electrode and counter electrode, the coating including a reagent coating for triglycerides. In one alternative, the coating includes a surfactant and a triglyceride hydrolyzing reagent. The coating further includes Glycerol kinase and Glycerol-3-phosphate dehydrogenase. The coating further includes a coenzyme and a redox agent capable of being oxidized or reduced to form a product. In one configuration, the triglyceride hydrolyzing reagent is lipoprotein lipase. Optionally, the coenzyme is NAD. Alternatively, the surfactant includes a bile acid derivative. In one configuration, the surfactant includes a salt of a bile acid derivative.

In another embodiment, a reagent mixture for an electrochemical triglyceride sensor includes a triglyceride hydrolyzing reagent. The reagent mixture further includes Glycerol kinase and Glycerol-3-phosphate dehydrogenase. The reagent mixture further includes a coenzyme and a redox agent capable of being oxidized or reduced to form a product. In one alternative, the reagent mixture further includes a surfactant. Alternatively, the triglyceride hydrolyzing reagent is lipoprotein lipase. Optionally, the coenzyme is NAD. Alternatively, the surfactant includes a bile acid derivative. Optionally, the surfactant includes a salt of a bile acid derivative.

In one embodiment, a system for the electrochemical detection of triglyceride levels includes a test strip including an electrode and a counter electrode, the electrode and counter electrode located proximate to a sample reception area. The system further includes a coating on one of the electrode and counter electrode, the coating including a reagent coating for triglycerides. The system further includes an analyzer for receiving the test strip and including instructions stored on a non-transitory medium for applying a current or a voltage to the test strip and responsively determining an amount of triglycerides. Optionally, the coating includes: a surfactant; a triglyceride hydrolyzing reagent; Glycerol kinase; Glycerol-3-phosphate dehydrogenase; a coenzyme; and a redox agent capable of being oxidized or reduced to form a product. Alternatively, the triglyceride hydrolyzing reagent is lipoprotein lipase. Optionally, the coenzyme is NAD. In one configuration, the surfactant includes a bile acid derivative. In another configuration, the surfactant includes a salt of a bile acid derivative.

In one embodiment, a method of detecting triglycerides includes providing an electrochemical test strip and placing the electrochemical test strip in an analyzer. The method further includes placing a blood sample on the electrochemical test strip; measuring a current provided through the blood sample and the electrochemical test strip; and calculating a level of triglycerides with the analyzer based on the current. Optionally, the test strip includes an electrode and a counter electrode, the electrode and counter electrode located in a sample reception area; and a coating on one of the electrode and counter electrode, the coating including a reagent coating for triglycerides. Alternatively, the coating includes a surfactant; a triglyceride hydrolyzing reagent; Glycerol kinase; Glycerol-3-phosphate dehydrogenase; a coenzyme; and a redox agent capable of being oxidized or reduced to form a product. Optionally, the triglyceride hydrolyzing reagent is lipoprotein lipase. Alternatively, the coenzyme is NAD. Optionally, the surfactant includes a bile acid derivative. In one configuration, the surfactant includes a salt of a bile acid derivative.

DETAILED DESCRIPTION

Figure 1:
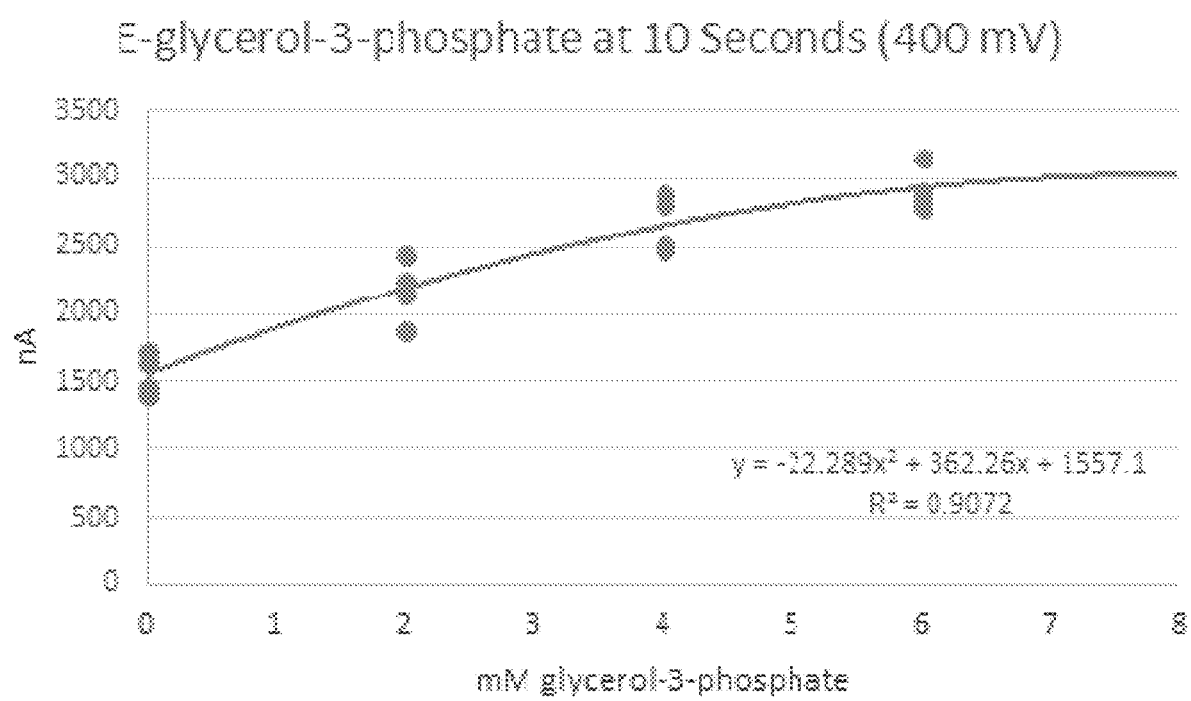
FIG. 1 shows a proof-of-concept graph that was produced.

Certain terminology is used herein for convenience only and is not to be taken as a limitation on the embodiments of the systems and methods for electrochemical triglyceride assays. In the drawings, the same reference letters are employed for designating the same elements throughout the several figures.

In many embodiments, the intended use may be to test whole blood. There are many advantages provided by an electrochemical triglyceride assay, as compared to an optical assay. In contrast to many optical assays, by having an amperometric triglyceride assay, no membranes are necessary. Many current optical assays are dependent on different membrane manufacturers which discontinue membranes at their discretion.

Calibration of the analyzer may be easier with electrochemical testing. Measuring current (nA) is a standardized process, whereas standardizing reflectance is more difficult.

Testing electrochemically for triglycerides may result in a cheaper cost per test strip due to less reagent, less raw materials (membranes, strip carriers, etc.), and automation of the process. Electrochemical test strips are generally inexpensive to produce due to the automation and small amounts of reagent used. The proposed electrochemical triglyceride assay is not dependent on oxygen and, thus, can test both venous and capillary blood.

Testing triglycerides via electrochemistry may, in many configurations, result in better precision than optical tests.

The test range of an electrochemical triglyceride assay may be larger than a reflectance assay in many embodiments. Reflectance tests are limited at the high concentrations by the amount of color that can be generated. However, electrochemical assays are able to measure much higher concentrations. This would be beneficial for the triglyceride assay, as we have had requests from those experimenting with animals to have a triglyceride range to 1000 mg/dL or more.

In some embodiments, the sample size will be small: ~1.2 µL instead of 15 µL as is used in an optical system. In many embodiments, a transfer pipette is not needed to apply blood to a strip, since the blood sample simply is wicked into the sampling port.

The triglyceride concentration in blood is an important analyte for healthcare providers to test. High blood pressure, obesity, heart disease, and diabetes are all correlative to high triglyceride levels. In addition, testing triglycerides with total cholesterol and HDL will allow for the calculation of LDL. By having an electrochemical triglyceride assay, a foundation has been laid to create a full electrochemical lipid panel.

The following reaction below is one embodiment of a reaction for creating an electrochemical triglyceride test. We have demonstrated proof of concept of reactions 3 and 4. Reactions 1 and 2 currently are practiced in the PTS reflectance test strip and, based on these results, will work when fully optimized from the last equation on up.

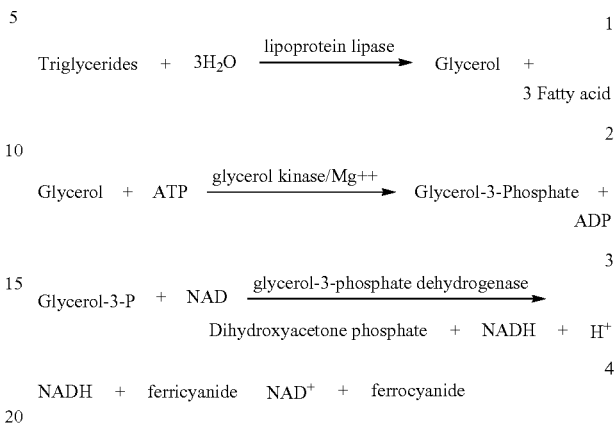

An alternative to using diaphorase may be to incorporate Dojindo's 1-methoxy PMS mediator. Also, other mediators more conducive to alkaline conditions may be used in place of potassium ferricyanide.

A key aspect of embodiments of an electrochemical test strip for triglycerides is using glycerol-3-phosphate dehydrogenase. In many embodiments, the enzyme glycerol-3-phosphate dehydrogenase has shown that there is potential for an assay. Further optimization of pH, concentration of reactants, experimentation with mediators, etc., will yield better precision, greater slope, and lower intercept for a triglyceride assay. Provided herein is proof of concept of an electrochemical triglyceride assay.

FIG. 1 shows a proof-of-concept of electrochemical strip that was made to test glycerol-3-phosphate solutions in glycine buffer pH 9. Further optimization should allow for a lower intercept, better slope, and better precision.

In addition to having an amperometric triglyceride sensor, in some embodiments, it is possible to incorporate a previous invention using a versatile electrochemical test strip and offer multiple tests with the triglyceride test. While the triglycerides are tested, it may be helpful to check other important analytes such as glucose, cholesterol, HDL, etc.

Figure 2:
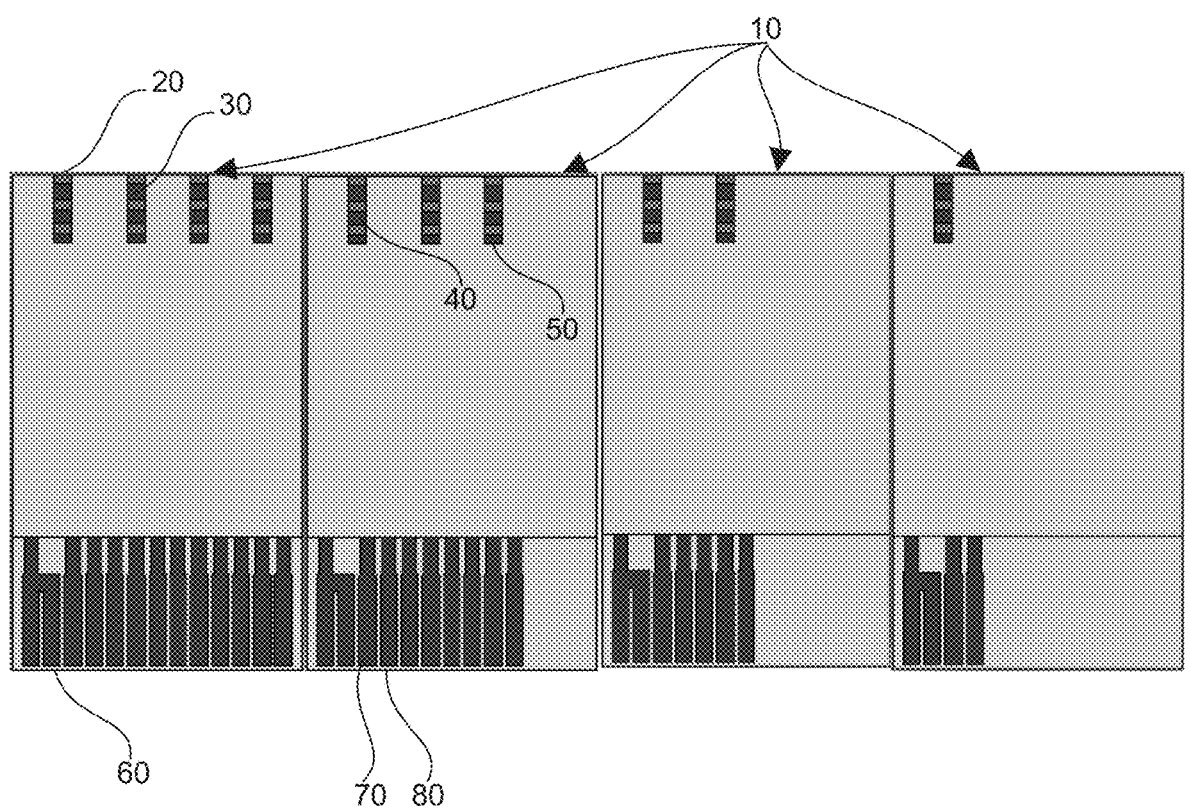
FIG. 2 shows one embodiment of the strip design.

FIG. 2 shows one embodiment of the strip design including a triglycerides detector. Shown are four strips 10. From left to right, the strips 10 have 4, 3, 2, and 1 sample receiving ports 20. Each sample receiving port 20 may have an electrode 30, a counter electrode 40, and a reference electrode 50. The reference electrode 50 may provide for a fill indication, as it will only pass a voltage when the sample reaches the electrode 50. The contacts 70, 80 also are visible, which interconnect with the electrodes and connect to contacts in the analyzer when inserted. The strip size does not change depending on the number of assays. In addition, the electrode placement does not change depending on the type of assays. Depending on what is desired for the testing scheme, sheets are printed for one, two, three, or four analytes. The spirit behind this invention disclosure is not to limit the size of the panel to only four analytes, but to provide a concept that is protected whether one or ten analytes are tested. Also, the electrodes do not all need to be on one side of the strip. Superior technology may be able to place electrodes on both sides of the strip, thus allowing for miniaturization.

In some embodiments, single analyte test strips are designed to have the same location with at least four associated electrodes. The electrode 60 that appears as an "h" is used for strip detection by the analyzer. The remaining assays will have at least three electrodes—one for sample fill detection, and the other two as a counter electrode and a working electrode. These assays are not limited to a set number of electrodes, for it is foreseen in some embodiments that more electrodes may be added for purposes of determining and correcting for hematocrit or other interfering substances.

In multiple configurations, reagents may be painted on the electrodes. Alternatively, reagents may be printed, coated, dip coated, or otherwise applied, as will be apparent in the field. Various types of electrodes may be used as well, including those made of carbon, gold, platinum, copper, or other conductive materials, as will be apparent to those in the field.

FIG. 2 displays separate blood sampling ports for each assay. Some embodiments may include separate sampling ports, particularly if there could be "cross talk" between reagents. In summary, embodiments of a novel idea for an electrochemical triglyceride assay have been presented. It is demonstrated that an electrochemical reaction with glycerol-3-phosphate and a mediator is a viable testing technique. An electrochemical triglyceride assay will have a smaller sample size, shorter test time, better precision, and will be cheaper to manufacture.

Many animal testing laboratories have requested the ability to test triglycerides at values around 1000 mg/dL. While this kind of a range is difficult for a reflectance test, an electrochemical test can easily test high concentrations. This test could be advantageous for rat, mice, rabbit, etc., testing when the amount of blood taken is critical.

Provided are multiple embodiments of an electrochemical triglyceride assay. A strip for checking triglyceride levels is a convenient point-of-care (POC) assay, but it is best when married to a cholesterol and HDL test to form a lipid panel. We have shown evidence of the first building block to an electrochemical lipid panel. Building an electrochemical lipid panel will overwhelm the competition in the POC market. An electrochemical lipid panel will have a smaller sample size, shorter test time, better precision, and will be cheaper to manufacture.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof. Note that, although particular embodiments are shown, features of each attachment may be interchanged between embodiments.

The invention claimed is:

1. A system for the electrochemical detection of triglyceride levels, the system comprising:
    a test strip including an electrode and a counter electrode, the electrode and counter electrode located proximate to a sample reception area;
    a coating on one of the electrode and counter electrode, the coating including a reagent coating for triglycerides, the regent coating comprising a surfactant, a triglyceride hydrolyzing reagent, glycerol kinase, adenosine triphosphate, glycerol-3-phosphate dehydrogenase, a coenzyme, and a redox agent capable of being oxidized or reduced to form a product; and
    an analyzer for receiving the test strip and including instructions stored on a non-transitory medium for applying a current or a voltage to the test strip and responsively determining an amount of triglycerides, wherein the redox agent is ferricyanide and an enzyme, wherein the enzyme is diaphorase, to catalyze a redox reaction.

2. The system of claim 1, wherein the triglyceride hydrolyzing reagent is lipoprotein lipase.

3. The system of claim 1, wherein the coenzyme is nicotinamide adenine dinucleotide (NAD).

4. The system of claim 1, wherein the surfactant includes a bile acid derivative.

5. The system of claim 1, wherein the surfactant includes a salt of a bile acid derivative.

6. A method of detecting triglycerides, the method comprising:
    providing an electrochemical test strip, the test strip including an electrode and a counter electrode, the electrode and counter electrode located in a sample reception area, and a coating on one of the electrode and counter electrode, the coating including a reagent coating for triglycerides, the reagent coating comprising a surfactant, a triglyceride hydrolyzing reagent, glycerol kinase, adenosine triphosphate, glycerol-3-phosphate dehydrogenase, a coenzyme, and a redox agent capable of being oxidized or reduced to form a product;
    placing the electrochemical test strip in an analyzer;
    placing a blood sample on the electrochemical test strip;
    measuring a current provided through the blood sample and the electrochemical test strip; and
    calculating a level of triglycerides with the analyzer based on the current, wherein the redox agent is ferricyanide and an enzyme, wherein the enzyme is diaphorase, to catalyze a redox reaction.

7. The method of claim 6, wherein the triglyceride hydrolyzing reagent is lipoprotein lipase.

8. The method of claim 6, wherein the coenzyme is nicotinamide adenine dinucleotide (NAD).

9. The method of claim 6, wherein the surfactant includes a bile acid derivative.

10. The method of claim 6, wherein the surfactant includes a salt of a bile acid derivative.

* * * * *